(12) United States Patent
Cohen et al.

(10) Patent No.: US 11,707,189 B1
(45) Date of Patent: Jul. 25, 2023

(54) METHODS, DEVICES AND SYSTEMS FOR CLEANING AN IMAGING ELEMENT WITH A TRANSLATABLE CLEANING ELEMENT

(71) Applicant: ClearCam Inc., Austin, TX (US)

(72) Inventors: Alexander Ross Cohen, Austin, TX (US); Christopher Robert Idelson, Austin, TX (US); Jonathan Richmond Hearn, Colleyville, TX (US)

(73) Assignee: ClearCam Inc., Austin, TX (US)

( * ) Notice: Subject to any disclaimer, the term of this patent is extended or adjusted under 35 U.S.C. 154(b) by 0 days.

(21) Appl. No.: 17/979,186

(22) Filed: Nov. 2, 2022

Related U.S. Application Data (60) Provisional application No. 63/308,544, filed on Feb. 10, 2022.

(51) Int. Cl.
| | |
|---|---|
| *A61B 90/70* | (2016.01) |
| *A61B 1/12* | (2006.01) |
| *A61B 1/313* | (2006.01) |
| *B08B 1/00* | (2006.01) |

(52) U.S. Cl.
CPC ............ *A61B 1/126* (2013.01); *A61B 1/3132* (2013.01); *B08B 1/006* (2013.01); *B08B 1/008* (2013.01)

(58) Field of Classification Search
None
See application file for complete search history.

(56) References Cited

U.S. PATENT DOCUMENTS

| | | |
|---|---|---|
| 5,392,766 A | 2/1995 | Masterson et al. |
| 5,518,502 A | 5/1996 | Kaplan et al. |
| 5,695,448 A | 12/1997 | Kimura et al. |
| 6,755,782 B2 | 6/2004 | Ogawa |
| 6,923,759 B2 | 8/2005 | Kasahara et al. |

(Continued)

FOREIGN PATENT DOCUMENTS

| | | |
|---|---|---|
| CN | 101883531 B | 7/2014 |
| EP | 0647425 A1 | 4/1995 |

(Continued)

OTHER PUBLICATIONS

Translation of JP2007-117289 by Fukuda, published May 17, 2007.*

*Primary Examiner* — Mikhail Kornakov
*Assistant Examiner* — Ryan L Coleman
(74) *Attorney, Agent, or Firm* — IVC Patent Agency; David O. Simmons (57) ABSTRACT

A device operable to clean an imaging element of a visualization scope comprises a visualization scope engagement body, a cleaning element having a first end portion thereof located adjacent to a distal end of the visualization scope engagement body and a cleaning head attached to the visualization scope engagement body at the distal end thereof. The first end portion of the cleaning element is engaged with the cleaning head. The cleaning head is movable between a deployed configuration relative to the visualization scope engagement body and a retracted configuration relative to the visualization scope engagement body. A centerline longitudinal axis of the visualization scope engagement body extends through the cleaning head when the cleaning head is in the deployed configuration and does not extend through the cleaning head when the cleaning head is in the retracted configuration. The cleaning element is movable for cleaning debris from the imaging element.

16 Claims, 7 Drawing Sheets

(56) References Cited

U.S. PATENT DOCUMENTS

| | | |
|---|---|---|
| 7,959,561 B2 | 6/2011 | Akui et al. |
| 8,690,764 B2 | 4/2014 | Clark et al. |
| 8,979,738 B2 | 3/2015 | Hsu et al. |
| 9,050,036 B2 | 6/2015 | Poll et al. |
| 9,486,129 B2 | 11/2016 | Rodriguez Sanjuan |
| 9,763,567 B2 | 9/2017 | O'Prey et al. |
| 10,791,918 B1 | 10/2020 | Gilkey et al. |
| 2002/0065450 A1* | 5/2002 | Ogawa ................ A61B 1/126 600/157 |
| 2009/0229067 A1 | 9/2009 | Becker et al. |
| 2009/0250081 A1 | 10/2009 | Gordin et al. |
| 2012/0101338 A1 | 4/2012 | O'Prey et al. |
| 2014/0094650 A1 | 4/2014 | Schaning |
| 2016/0128551 A1 | 5/2016 | Hsu et al. |
| 2016/0143512 A1 | 5/2016 | Cheng et al. |
| 2017/0332893 A1 | 11/2017 | Irion et al. |
| 2017/0367571 A1 | 12/2017 | Nave |
| 2018/0344427 A1* | 12/2018 | Rosenbaum ........... A61B 90/70 |

FOREIGN PATENT DOCUMENTS

| | | |
|---|---|---|
| JP | S5861723 A | 4/1983 |
| JP | H01204637 A | 8/1989 |
| JP | 04-362912 | 12/1992 |
| JP | H05103748 A | 4/1993 |
| JP | 2007-117289 * | 5/2007 |
| JP | 5735908 B2 | 6/2015 |
| WO | 2014034839 A1 | 3/2014 |
| WO | WO2017006684 | 12/2017 |
| WO | 2020112852 A1 | 4/2020 |

* cited by examiner

METHODS, DEVICES AND SYSTEMS FOR CLEANING AN IMAGING ELEMENT WITH A TRANSLATABLE CLEANING ELEMENT

FIELD OF THE DISCLOSURE

This patent application claims priority from U.S. Provisional Patent Application having Ser. No. 63/308,544, filed 10 Feb. 2022, entitled "METHODS, DEVICES AND SYSTEMS FOR CLEANING AN IMAGING ELEMENT WITH A TRANSLATABLE CLEANING ELEMENT," having a common applicant herewith and being incorporated herein in its entirety by reference.

FIELD OF THE DISCLOSURE

The disclosures made herein relate generally to cleaning of apparatuses that utilize an imaging element for visualization of structures within a concealed operative site and, more particularly, to methods, devices and systems for cleaning an exposed surface of the imaging element while the exposed surface is located within a concealed operative site such as, for example, an in-vivo human or animal environment.

BACKGROUND

Surgical procedures utilizing in-vivo visualization of target surgical sites are well known as a form of a concealed operation site. Examples of these surgeries include, but are not limited to, endoscopic surgery, laparoscopic surgery, thoracoscopic surgery and the like. These surgical procedures all utilize a surgical instrument having an integrated visualization apparatus for providing in-vivo visualization of a target surgical site within a surgical space of the patient. Although it is common for the surgical instrument to be referred to in the context of the specific type of surgical procedure (e.g., endoscope for endoscopic surgery, laparoscope for laparoscopic surgery, and the like), these surgical instruments are generally referred to herein as an "endoscope".

Figure 1:
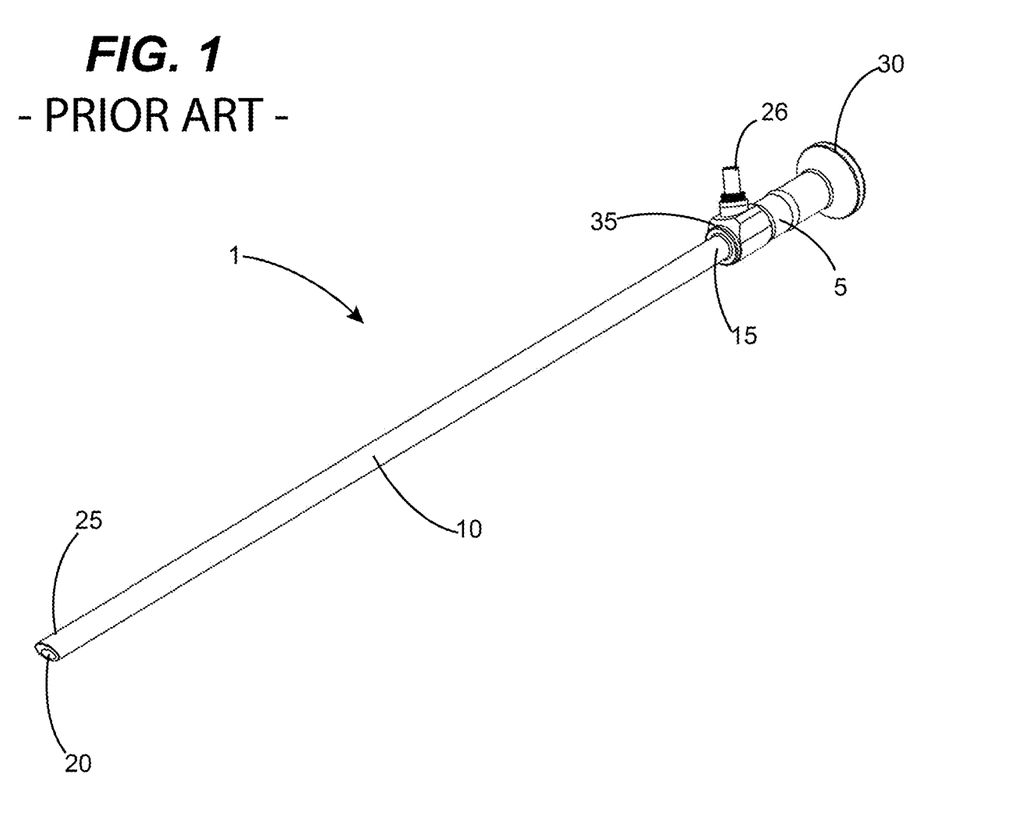
FIG. 1 is a perspective view showing a prior art visualization scope.

As shown in FIG. 1, an endoscope 1 (i.e., a visualization apparatus) used in these surgical procedures is characterized as having a user interface portion 5 and an extension portion 10 connected at its proximate end 15 to the user interface portion 5. Scopes for endoscopic surgery generally have an extension portion that is substantially flexible, whereas scopes for other types of surgical procedures—e.g., for laparoscopic surgery, as shown in FIG. 1—generally have an extension portion 10 that is substantially rigid. The extension portion 10 has an imaging element 20 such as a lens at its distal end portion 25. It is well-known that the extension portion 10 may have an angled end face (e.g., 135-degree) or a flat end face (nominally 0-degree), shown. The imaging element 20 can have an exposed surface that is typically generally flush with or that defines an end face of the extension portion 10. The imaging element 20 is connected to an optical fiber or other image transmitting element that is internal to the endoscope. The optical fiber or other image transmitting element extends along the length of the extension portion 10 and terminates at an eyepiece 30 on the user interface portion 5. The eyepiece 30 enables the imaging element 30 to be connected to a visualization system (e.g., a camera connected to a visual display console) through which target surgical sites can be viewed by surgery personnel.

During a surgical procedure using an endoscope, the exposed surface of the imaging element thereof may become impaired due to one or more in-vivo scenarios. Examples of these scenarios include the exposed surface of the imaging element becoming fogged with moisture within the surgical space, or the exposed surface of the imaging element may be smeared by blood or other bodily fluids or tissues (e.g. interstitial fluid, fat tissue or the like). Currently, there are two primary different endoscope cleaning methods that are commonly utilized. The first of these cleaning methods is to remove the endoscope from the body, wipe the imaging element clean, and reinsert the endoscope into the body. This method, though effective, is time consuming and causes the surgeon to lose visual of the surgical site, which can be considered dangerous, as surgical instruments typically remain inside the body. This method can also subject the patient to a higher risk of infection. The second of these cleaning methods is to wipe the exposed surface of the imaging element upon a nearby organ or tissue. Although the endoscope remains inside the body, takes less time to clean and does not potentially compromise the surgical site, this method is often not sufficiently effective either due to the "cleaning" surface not providing effective cleaning performance or simply further contaminating the exposed surface of the imaging element. Also, when using either of these cleaning methods, the surgeon must undesirably spend time relocating the endoscope to the surgical site after cleaning the imaging element.

At a minimum, current approaches for cleaning the exposed surface of the imaging element can be a hindrance and an annoyance for surgeons and may offer poor cleaning performance. Additionally, the action of cleaning the exposed surface of the imaging element may increase the length of time a surgical procedure takes, thereby decreasing the amount of operating room (OR) time available to the hospital. It may also be costly for hospitals, patients, and insurance companies due to wasted time, and possibly surgical complications and post-surgical infection rates. Additionally, as patients undergo longer procedures, their time spent under anesthesia increases. Increased time under anesthesia has been shown to correlate to a rise in surgical complication rates and post-surgical infection rates. Thus, added time that may be associated with current commonly used approaches for cleaning the exposed surface of the imaging element is not only a hindrance, but also potentially medically and financially costly.

Thus, to maintain required visualization of target surgical sites, it is desirable to clean an exposed surface of an imaging element of a visualization apparatus while the distal end portion of the visualization apparatus remains in a concealed operation site (e.g., an endoscope in-vivo). Therefore, methods, devices and systems that provide an effective, efficient, simple and reliable approach for cleaning an exposed surface of an imaging element of a visualization apparatus (e.g., visualization scope such as an endoscope) while the distal end portion of visualization apparatus is still within the concealed operation site (e.g., in-vivo) would be advantageous, desirable and useful.

SUMMARY OF THE DISCLOSURE

Embodiments of the disclosures made herein are directed to methods, devices and systems that provide an effective and reliable approach for cleaning an exposed surface of an imaging element (e.g., a lens) of a visualization apparatus (e.g., visualization scope such as an endoscope) while the distal end portion of the visualization apparatus is within a concealed operational site (e.g., in-vivo). More specifically, one or more embodiments of the disclosures made herein provide a cleaning device for use with an endoscope utilized in one or more types of surgical procedures (e.g., endoscopic surgery, laparoscopic surgery, thoracoscopic surgery and the like), The cleaning device incorporates a cleaning element such as an absorbent or otherwise contaminant-receptive length of cleaning material (e.g., a ribbon, belt or strip of material) used for cleaning the exposed surface of the imaging element of the visualization apparatus while the imaging element is within the concealed operation site. In preferred embodiments, the cleaning material (i.e., element) is selectively translatable over an imaging element of the visualization apparatus. The cleaning device is preferably adapted for having the visualization apparatus engaged therewith (e.g., mounted thereon) but can also be entirely or partially integral with one or more components of a system comprising a visualization apparatus (e.g., a robotic arm configured for carrying, operating and manipulating an endoscope).

In one or more embodiments, a device operable to clean an imaging element of a visualization scope comprises a visualization scope engagement body, a cleaning element having a first end portion thereof located adjacent to a distal end of the visualization scope engagement body and a cleaning head attached to the visualization scope engagement body at the distal end thereof. The first end portion of the cleaning element is engaged with the cleaning head. The cleaning head is movable between a deployed configuration relative to the visualization scope engagement body and a retracted configuration relative to the visualization scope engagement body. A centerline longitudinal axis of the visualization scope engagement body extends through the cleaning head when the cleaning head is in the deployed configuration and does not extend through the cleaning head when the cleaning head is in the retracted configuration.

In one or more embodiments, a device operable to clean an imaging element of a visualization scope comprises a visualization scope engagement body, a cleaning head and a cleaning element. An extension portion of the visualization scope is engageable the visualization scope engagement body for enabling the extension portion to be moveable between a plurality of positions relative to a distal end of the visualization scope engagement body. The cleaning head is attached to the visualization scope engagement body at the distal end thereof. The cleaning head is movable between a deployed configuration relative to the visualization scope engagement body and a retracted configuration relative to the visualization scope engagement body in conjunction with movement of the extension portion of the visualization scope between a first one of the positions and a second one of the positions different than the first one of the positions. The cleaning element has a first end portion thereof located adjacent to the distal end of the visualization scope engagement body. The first portion of the cleaning element is engaged with the cleaning head. The cleaning element is in contact with the imaging element when the cleaning head is in the deployed configuration and is displaced away from being in contact with the imaging element when the cleaning head is in the retracted configuration.

In one or more embodiments, a device operable to clean an imaging element of a laparoscope comprises a tubular body, a cleaning head, a drive unit and a cleaning element. The tubular body has a central passage within which an extension portion of a laparoscope is slidably engageable for enabling the extension portion to be axially moveable between a retracted configuration relative to the laparoscope and a deployed configuration relative to the laparoscope. The cleaning head includes a main body pivotably attached to the tubular body at the distal end thereof and a first cleaning element support body attached to the main body. The cleaning head is movable between a deployed configuration relative to the tubular body and a retracted configuration relative to the tubular body. A centerline longitudinal axis of the central passage extends through the first cleaning element support body when the cleaning head is in the deployed configuration thereof and does not extend through the first cleaning element when the cleaning head is in the retracted configuration thereof. The cleaning head is in the deployed configuration thereof when the extension portion is in the deployed configuration thereof and is in the retracted configuration thereof when the extension portion is in the retracted configuration thereof. The drive unit is at a proximate end of the tubular body and includes a second cleaning element support body and an actuation member coupled to the second cleaning element support body. Movement of the actuation member causes an associated movement of the second cleaning element support body. The cleaning element has a first end portion thereof engaged with the first cleaning element support body and a second end portion thereof engaged with the second cleaning element support body such that movement of the cleaning head between the deployed configuration relative to the tubular body and the retracted configuration relative to the tubular body causes corresponding movement of the first end portion of the cleaning element and such that movement of the actuation member from a present position to a different position than the present position causes a corresponding movement of the cleaning element relative to the main body of the cleaning head.

In one or more embodiments, a method of cleaning an imaging element of a visualization scope comprises a plurality of steps. A step is performed for engaging an extension portion of a visualization scope with a visualization scope engaging body of an imaging element cleaning device. The imaging element cleaning device has a cleaning head including a main body moveably attached to the visualization scope engaging body at the distal end thereof and a first cleaning element support body attached to the main body. The imaging element cleaning device includes a cleaning element having a first end portion thereof engaged with the first cleaning element support body. A step is performed for axially positioning the extension portion for causing the cleaning head to become displaced from a deployed configuration relative to the relative to the visualization scope engaging body to a retracted configuration relative to the visualization scope engaging body. A step is performed for using the visualization scope for visualizing a target surgical site within a surgical space of a patient while the cleaning head is maintaining in the retracted configuration. For cleaning contaminants from the imaging element during use of the visualization scope, a step is performed for axially positioning the extension portion for causing the cleaning head to become displaced from the retracted configuration relative to the visualization scope engaging body to the deployed configuration relative to the visualization scope engaging body whereby the cleaning element is engaged with the imaging element. A step is performed for causing the cleaning element to move relative to the imaging element while the cleaning element is maintained in contact with the imaging element.

These and other objects, embodiments, advantages and/or distinctions of the present invention will become readily apparent upon further review of the following specification, associated drawings, and appended claims.

DETAILED DESCRIPTION

Figures 2, 3:
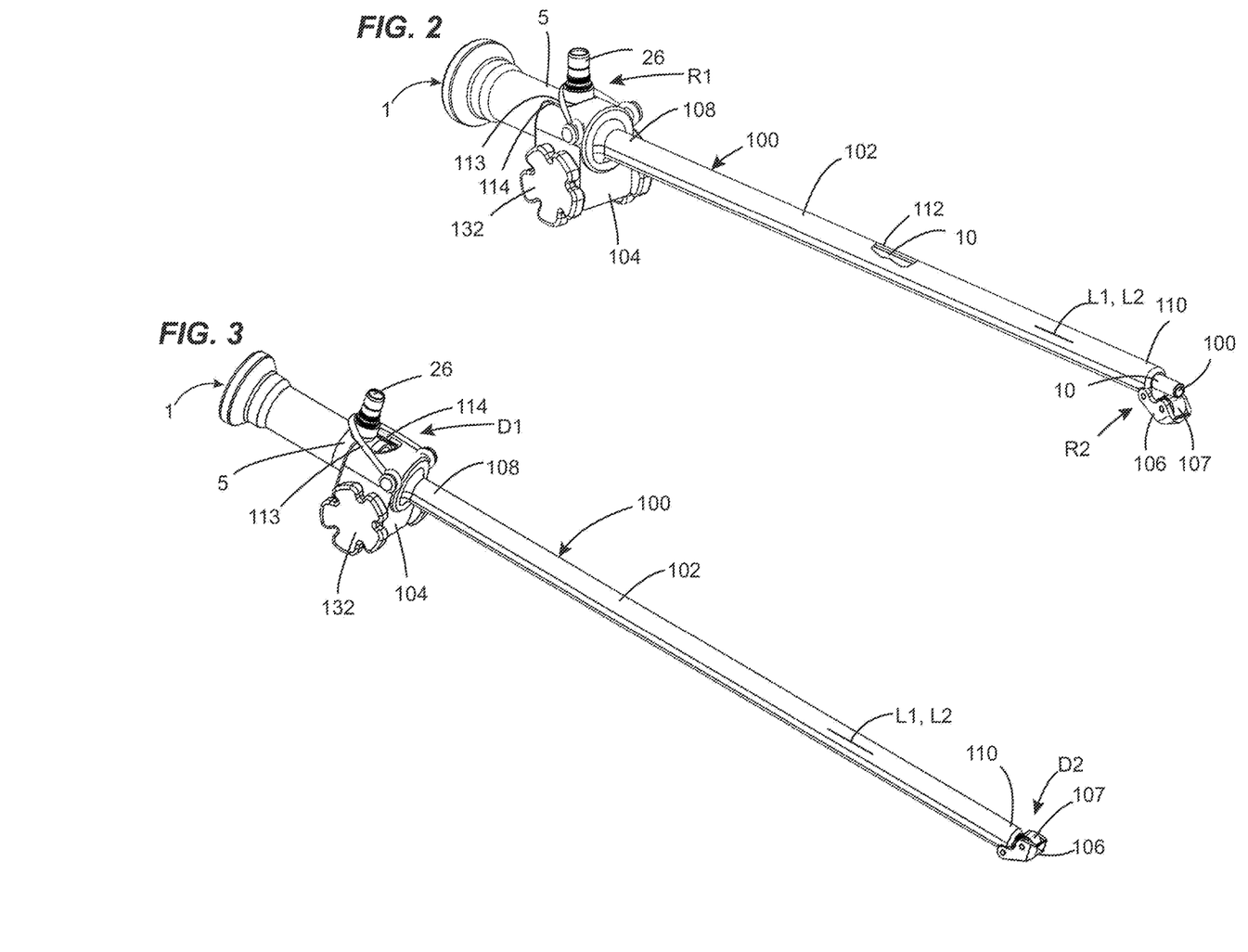
FIG. 2 is a perspective view showing a prior art visualization scope having an imaging element cleaning device in accordance with one or more embodiments of the disclosures made herein engaged therewith, wherein the imaging element cleaning device is in a retracted configuration enabling use of the visualization scope.
FIG. 3 is a perspective view showing a prior art visualization scope having the imaging element cleaning device of FIG. 2 engaged therewith, wherein the imaging element cleaning device is in a deployed configuration enabling cleaning of an imaging element of the visualization scope.
Figure 4:
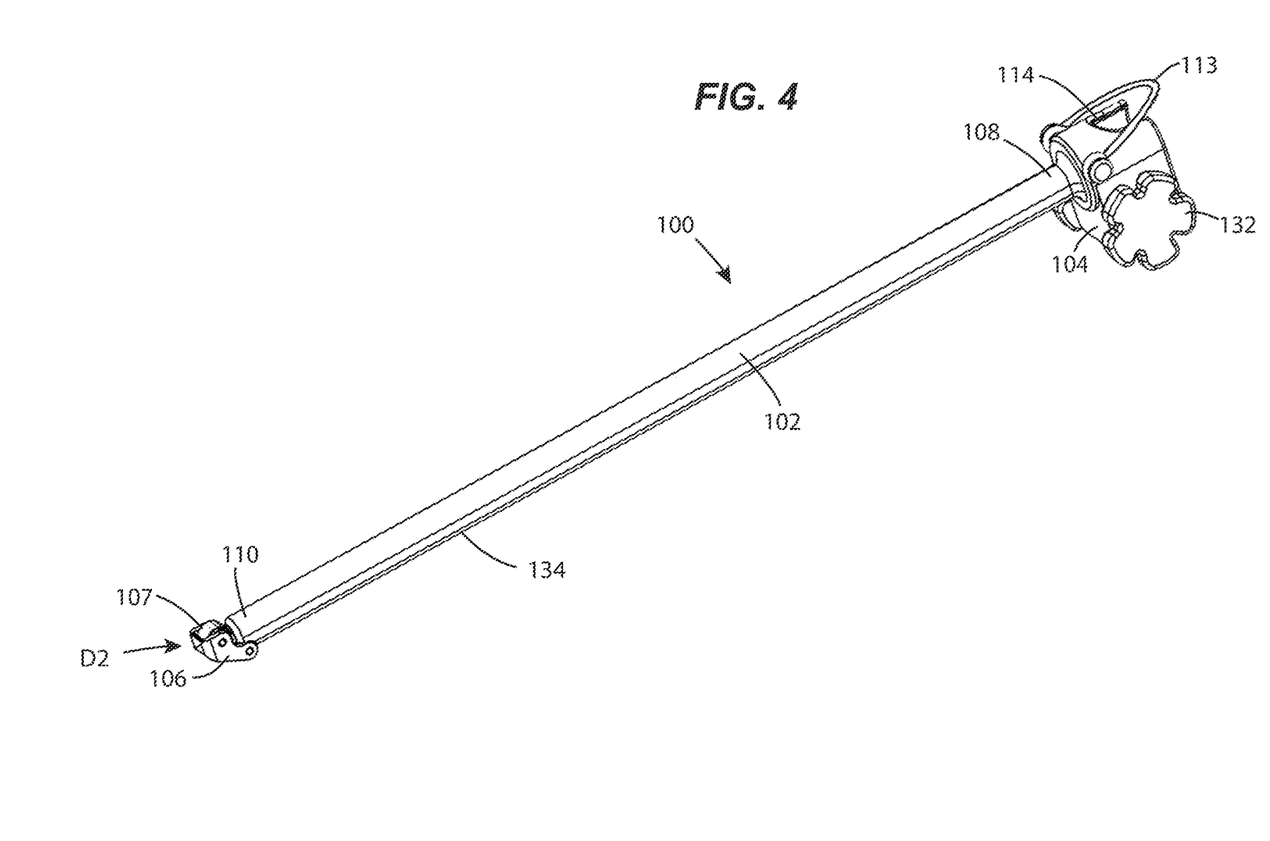
FIG. 4 is a perspective view of the imaging element cleaning device of FIG. 2.

FIGS. 2-4 show an imaging element cleaning device in accordance with one or more embodiments of the disclosures made herein (cleaning device 100). The cleaning device 100 is configured for being engaged with a visualization scope. For example, as shown in FIGS. 2 and 3, cleaning device 100 is engaged with the prior art visualization scope 1 discussed above in reference to FIG. 1.

Still referring to FIGS. 2-4, the cleaning device 100 comprises an elongated tubular body 102, a control body 104, a cleaning head 106 and a cleaning element 107. The control body 104 is attached (e.g., preferably fixedly) to the elongated tubular body 102 at its proximate end portion 108. The cleaning head 106 is preferably pivotably attached to the elongated tubular body 102 at its distal end portion 110. The extension portion 10 of the visualization scope 1 is positioned within a central passage 112 of the cleaning device 100. The user interface portion 5 of the visualization scope 1 is positioned within a mating receptacle of the control body 104. The central passage 112 of the cleaning device 100 extends through the elongated tubular body 102 and the control body 104. A centerline longitudinal axis L1 of the extension portion 10 of the visualization scope 1 extends approximately colinearly with a longitudinal reference axis L2 of the central passage 112. A resilient retention member 113 may be used for maintaining the visualization scope 1 and cleaning device 100 in engagement with each other.

The visualization scope 1 and the cleaning device 100 are jointly configured for enabling axial displacement between the visualization scope 1 and the cleaning device 100 along the longitudinal reference axes L1, L2. A reference portion 26 (e.g., light port) of the visualization scope 1 is located within a mating reference portion 114 to limit unrestricted rotational displacement between the visualization scope 1 and the cleaning device 100 while the visualization scope 1 is engaged with the cleaning device 100.

The cleaning device 100 is movable between a retracted configuration R1 (FIG. 2) and a deployed configuration D1 (FIG. 3) relative to the visualization scope 1. In preferred embodiments, the resilient retention member 113 urges the visualization scope 1 and the cleaning device 100 toward each other for causing the cleaning device 100 to be in its retracted configuration R1. In one or more embodiments, the cleaning device 100 may be adapted for enabling movement between its retracted configuration R1 and its deployed configuration D1 by manual manipulation of the visual scope 1 and the cleaning device 100. In one or more other embodiments, the cleaning device 100 may include a built-in mechanical mechanism or electro-mechanical mechanism through which a user can cause movement of the cleaning device 100 between its retracted configuration R1 and its deployed configuration D1. For example, the cleaning device may include a control member (e.g., mechanical or electro-mechanical) whose selection/movement causes an attached mechanical or electro-mechanical actuator to manipulate the visualization scope 1 and/or cleaning device 100 for causing transition of the cleaning device 100 from its retracted configuration R1 to its deployed configuration D1 relative to the visualization scope 1. In view of the disclosures made herein, a skilled person will appreciate one or more suitable prior art mechanism designs/concepts for enabling such configuration transition functionality.

When the cleaning device 100 is in the retracted configuration R1, the cleaning head 106 is in a corresponding retracted configuration R2 (FIG. 2) where the cleaning head 106 is outside of a field of view of the imaging element 20 of the visualization scope 1. When the cleaning device 100 moved to the deployed configuration D1, the cleaning head 106 is moved to a corresponding deployed configuration D2 (FIG. 3) where the cleaning head 106 is engaged with the imaging element 20 of the visualization scope 1 for enabling cleaning of the imaging element 20 by a cleaning element 107. The cleaning head 106 is urge toward the deployed configuration D2 such as by a resilient member (e.g., a spring or the like) for causing it to move from its retracted configuration R2 to its deployed configuration D2 in response to sufficient movement of the cleaning device 100 from its retracted configuration R1 to its deployed configuration D1 (or sufficient movement of the visualization scope 1 for causing cleaning device 100 to become transitioned from its retracted configuration R1 to its deployed configuration D1).

Figure 5:
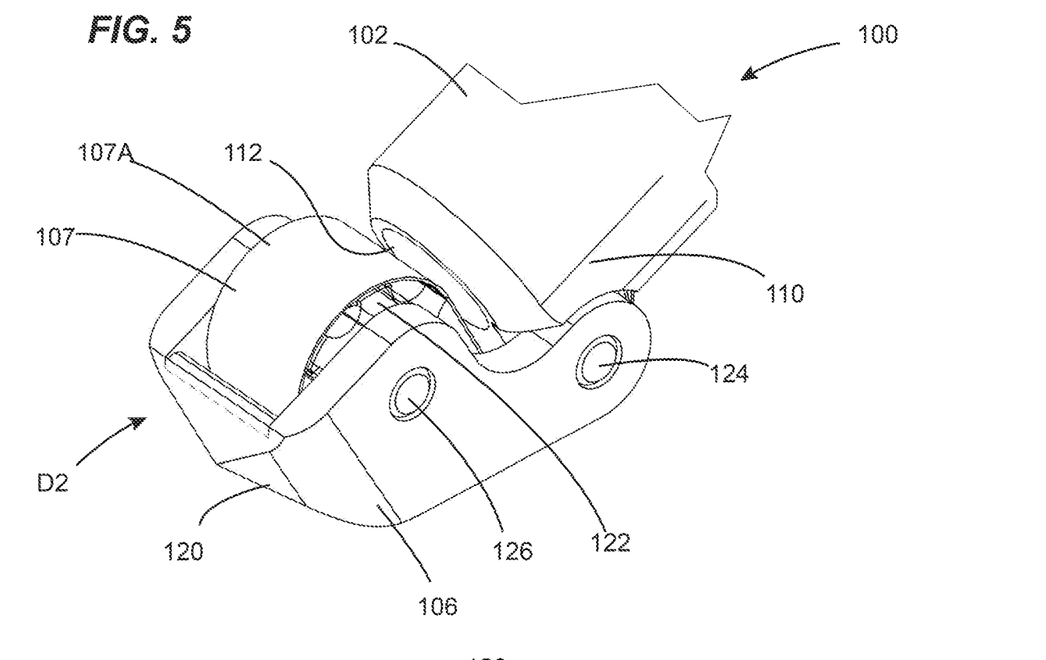
FIG. 5 is a first fragmentary perspective view of a distal end position of the imaging element cleaning device of FIG. 2.
Figure 6:
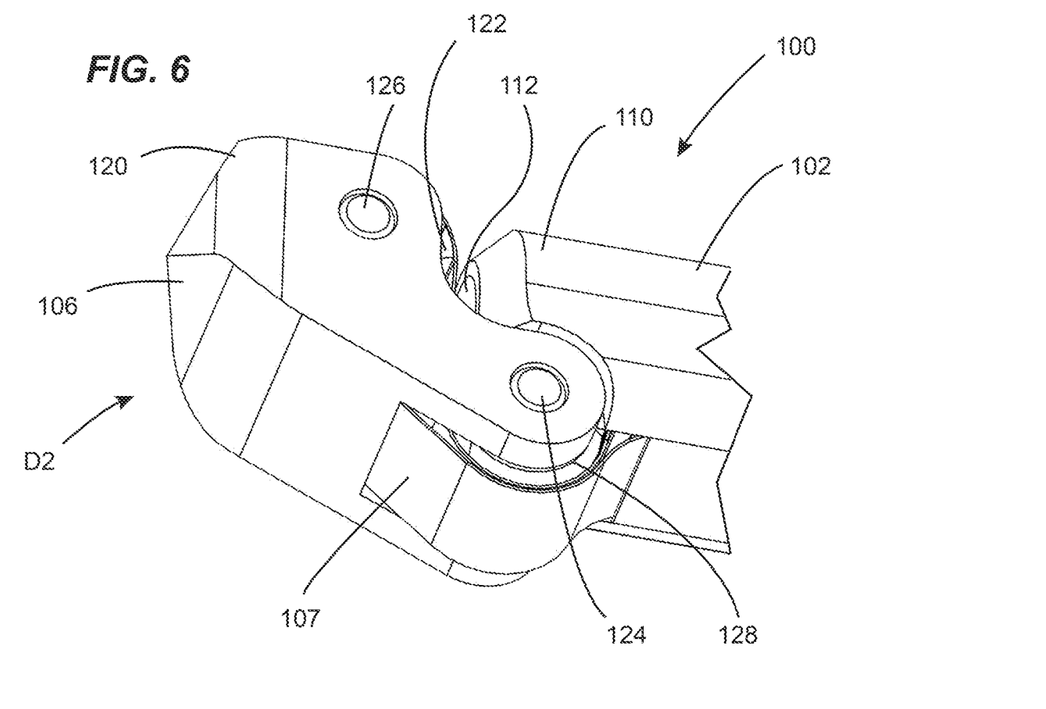
FIG. 6 is a second fragmentary perspective view of the distal end portion of the imaging element cleaning device of FIG. 2.
Figure 7:
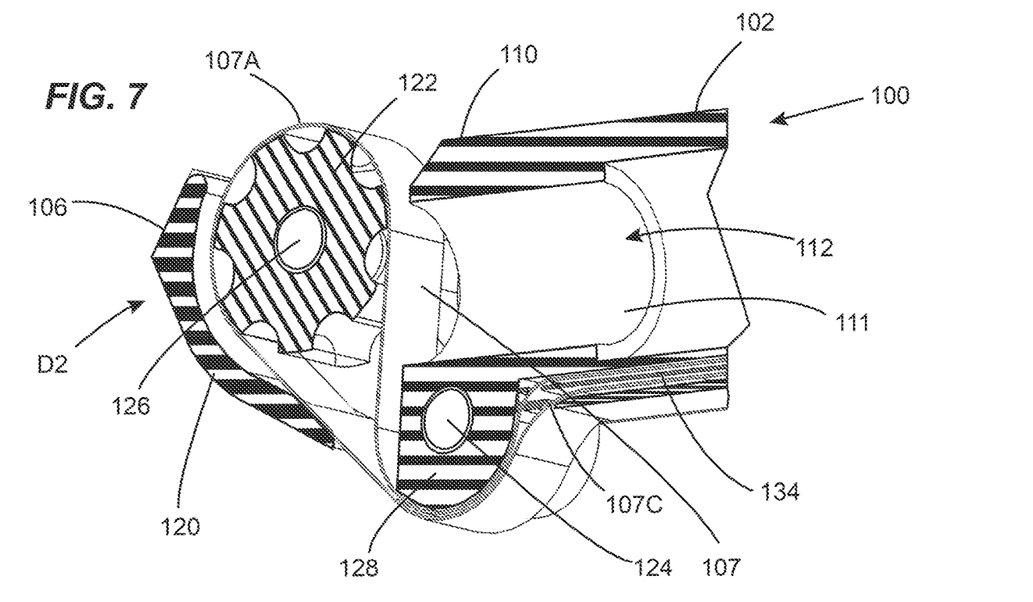
FIG. 7 is a cross-sectional fragmentary perspective view of the distal end portion of the imaging element cleaning device of FIG. 2.

As shown in FIGS. 5-7, the cleaning head 106 includes a main body 120 and a support body 122. The main body 120 is movable attached to the elongated tubular body 102 (e.g., pivotably via a pivot member 124). The support body 122 is attached to the main body 120 at a location on the main body 120 such that it is opposite the central passage 112 when the cleaning head 106 is in its deployed configuration D2. In one or more embodiments, the support body 122 is in the form of a roller that is rotatably attached to the main body 120 via a pin 126 for enabling rotation of the support body 122 relative to the main body 120. The outer surface of the support body 122 where it contacts the cleaning element 107 may have a profile or construction that enhances contact between the cleaning element 107 and the imaging element 20 of the visualization scope 1—e.g., flat, convex, concave, textures, multi-material etc. Optionally, the support body 122 may have a mounting portion that is attached to the main body 120 and a cleaning element engaging portion that is specifically adapted for supporting the cleaning element 106 and enabling required movement thereover—e.g., a compliant cleaning element engaging portion and a rigid mounting portion.

In one or more embodiments, the support body 120 may be in the form of a structure that does not roll or otherwise translate relative to a mounting member (e.g., a roller on a shaft). In such embodiments, the support member may be made to be compliant such as via use of elastomeric materials (e.g. foam, rubber) or a flexible geometrical design (e.g. a flexure mechanism). Compliance of the support member may also enable deformation of the cleaning element (e.g. cloth/ribbon) against scope surfaces of varying geometry, offering notable versatility, adaptability, and compatibility. A compliant support member may also engage with the cleaning element through material deformation and flexure engagement and further enable and/or actuate translation of the cleaning member along a desired pathway if and/or when actuated by a mechanism and/or user.

Methods of engagement between such a compliant support member and the cleaning element may exist through any suitable means (e.g., friction lock of wrap, pinch, or other mechanical constraint arrangement). In some embodiments, the compliant support member may engage with the cleaning member when actuated by a user through mechanisms internal to the device/system (i.e., active engagement). In some embodiments, the compliant support member may engage as an endoscope itself is translated within and relative to the device/system and comes into contact with the compliant member, ultimately engaging the compliant member with the cleaning element as a result of endoscope engagement (i.e., passive engagement).

Figure 8:
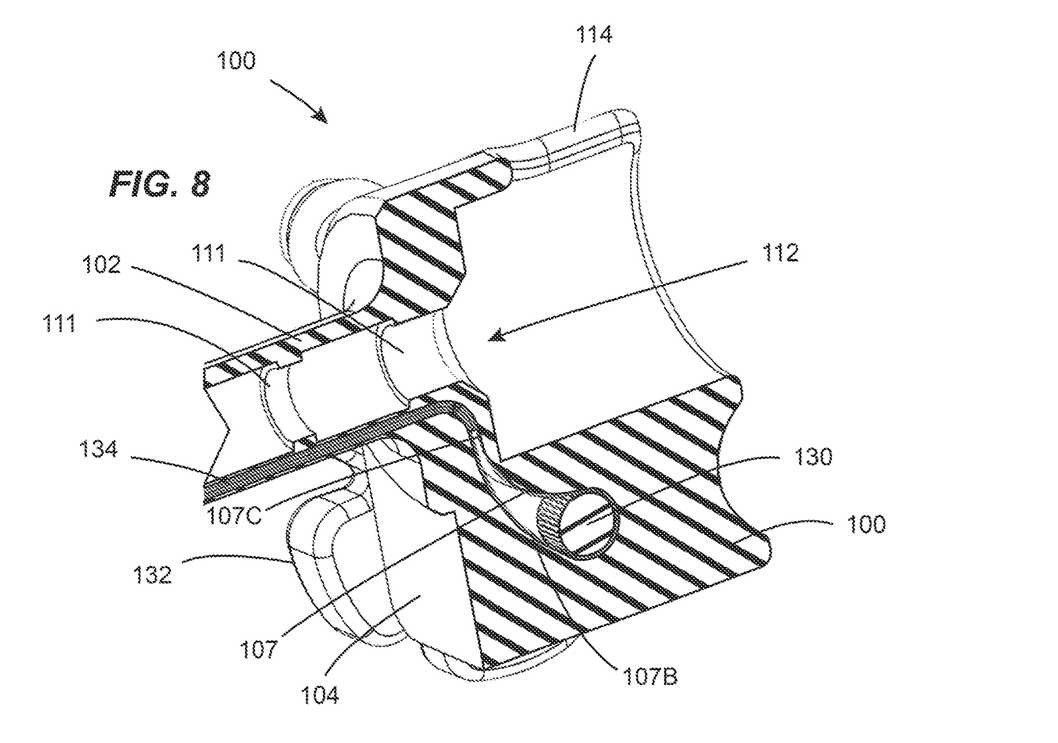
FIG. 8 is a cross-sectional fragmentary perspective view of a proximate end portion of the imaging element cleaning device of FIG. 2.

The elongated tubular body 102 may be configured for limiting friction between the extension portion 10 of the visualization scope 1 and mating inner surface of the elongated tubular body 102 (i.e., defined by the raised protrusions 111). Limiting friction aids in enabling movement of the cleaning device 100 between its retracted configuration R1 and its deployed configuration D1 relative to the visualization scope 1. For example, in one or more embodiments, as shown in FIGS. 7 and 8, the elongated tubular body 102 may include a plurality of spaced-apart raised protrusions 111 within the central passage 112 along is length. In one or more embodiments, the central passage 112 may had an inside diameter corresponding to the outside diameter of the extension portion 10 of certain visualization scope (e.g., nominal outside diameter of about 10 mm).

A cleaning device system in accordance with one or more embodiments of the disclosures made herein may include a reducer for enabling a visualization scope with an extension portion having an under-sized outside diameter to be operable engaged within the central passage 112 (e.g., nominal diameters of 10 mm). The reducer may include an extension portion-receiving segment having an outside diameter corresponding to the inside diameter of the central passage 112 (e.g., nominal outside diameter of about 10 mm) and having a concentric inside diameter corresponding to a visualization scope with an extension portion having an under-sized outside diameter (e.g., nominal outside diameter of about 5 mm). In this regard, a single cleaning device may be used with a plurality of different visualization scopes.

As discussed above, the cleaning head 106 is urge toward the deployed configuration D2 such as by a resilient member (e.g., a spring or the like) for causing it to move from its retracted configuration R2 to its deployed configuration D2 in response to sufficient movement of the cleaning device 100 from its retracted configuration R1 to its deployed configuration D1 (or sufficient movement of the visualization scope 1 for causing cleaning device 100 to become transitioned from its retracted configuration R1 to its deployed configuration D1). To this end, the main body 120 may be resiliently biased toward its deployed configuration D2. For example, a spring (not specifically shown) may urge the main body 120 toward its deployed configuration D2.

The cleaning element 107 is jointly engaged with the support body 122, a guide body 128 of the elongated tubular body 102, and a drive member 130 attached to the control body 104. As shown, the drive member 130 attached to the control body 104 is rotatable about a rotational axis and may have rotational force exerted thereon via rotational member 132 (e.g., knob) The cleaning element 107 may be in the form of a contiguous band—e.g., a unitary band or a length of material having opposing end thereof attached together.

As depicted in FIGS. 4-8, when the cleaning element 107 is in the form of a contiguous band, a first end portion 107A of the cleaning element 107 extends around the support body 122 and a second end portion 107B of the cleaning element 107 extends around the drive member 130. In one or more embodiments, the cleaning element 107 may be in the form of a length of material (i.e., cleaning element material) having a first end portion thereof attached to the drive member 130, where rotation of the drive member 130 causes the cleaning element material to be pulled from a source of supply (e.g., a supply roll of the cleaning element material). A central portion 107C of the cleaning element 107 may extend around the guide body 128 of the elongated tubular body 102 and a through a guide structure 134 (e.g., passage) of the elongated tubular body 102 and/or the control body 104.

In one or more embodiments of operation, the cleaning device 100 is engaged with the visualization scope 1 such that the cleaning head 106 is in its deployed orientation D2 and, correspondingly, the cleaning head 106 into its deployed orientation D2. The cleaning device 100 is then inserted, cleaning head 106 first, through an incision through a patient's tissue such that the cleaning device 100 serves as an obturator. Optionally, the cleaning device 100 can be inserted through the incision before engagement with the visualization scope 1. The cleaning device 100 is inserted to a depth where the tissue through which the incision is made encompasses the elongated tubular body 102. In this manner, the cleaning device 100 serves as a trocar. U.S. Pat. No. 11,033,179, which is incorporated herein in its entirety by reference, sets forth disclosure in regard to using respective portions of an imaging element cleaning device as an obturator and as a trocar.

The visualization scope 1 and the cleaning device 100 are then jointly manipulated for bringing the cleaning device 100 into its retracted orientation R1 and, correspondingly, the cleaning head into its retracted position R2 (FIG. 2), thereby enabling use of the visualization scope 1 to be used for remotely observing its in-vivo field of view. When cleaning of the imaging element 20 of the visualization scope 1 is necessary, the visualization scope 1 and the cleaning device 100 are jointly manipulated for bringing the cleaning device 100 into its deployed orientation D1 (FIG. 2) whereby the cleaning head 106 is engaged with (e.g., biased against, such as with a spring,) the imaging element 20 at the end face of the extension portion 20 of the visualization scope 1. In this manner, the rotational member 132 can be turned for causing blood or other bodily fluids or tissues (e.g. interstitial fluid, fat tissue or the like) to be cleaned from the surface of the imaging element 20 as the cleaning element translates relative to the imaging element 20.

Figure 9:
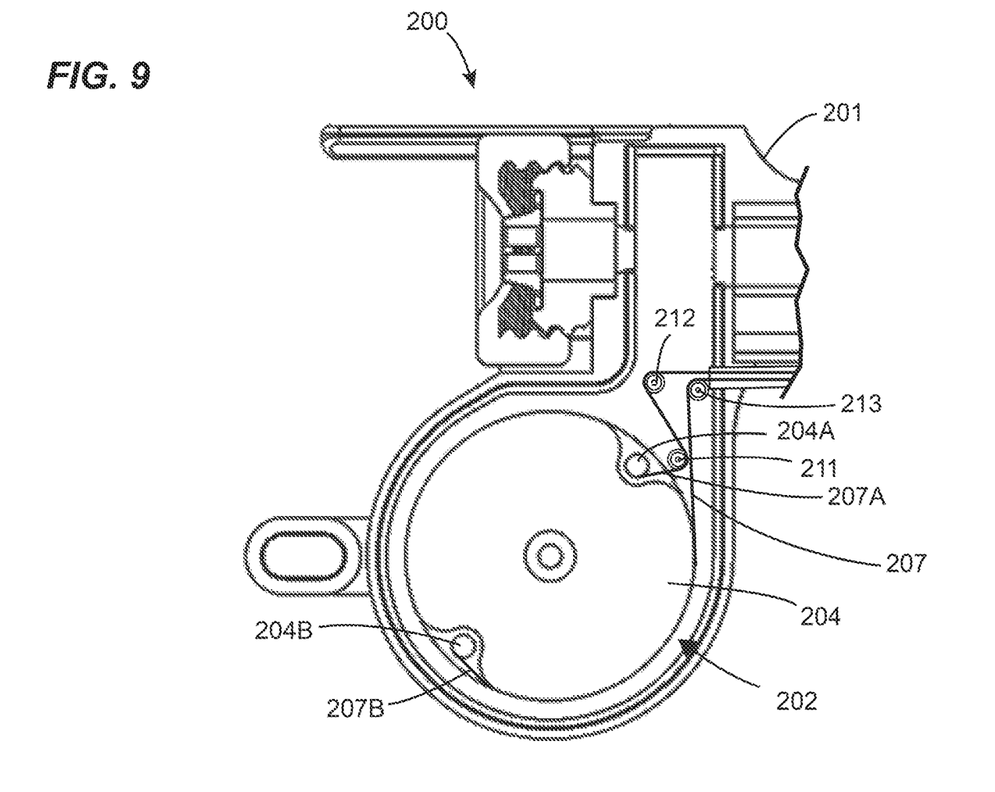
FIG. 9 is a diagrammatic view showing a cleaning element transport mechanism configured in accordance with a second embodiment of the disclosures made herein.

Cleaning devices in accordance with embodiments of the disclosures made herein are not limited to a particular mechanism for enabling a cleaning element to translate relative to an imaging element. For example, as shown in FIG. 9, cleaning device 200 having a cleaning element control mechanism 202. The cleaning element control mechanism 202 includes a rotatable body 204 (e.g., drum or spool) at the proximate end of the device 200 and a cleaning element 207. The rotatable body 204 is rotatably attached to a main body 201 of the device 200. The cleaning element 207 may be in the form of a length of material such as cloth, fabric, or other material or combinations of materials. The cleaning element 207 has free ends (i.e., cleaning element is not in the form of a band) whereby a first end portion 207A and a second end portion 207B are defined. The first end portion 207A of the cleaning element 207 is attached to a first attachment portion 204A of the rotatable body 204 and the second end portion 207B of the cleaning element 207 is attached to a second attachment portion 204B of the rotatable body 204. Preferably, the first and second attachment portions 204A, 204B of the rotatable body 204 are offset from each other by 180 degrees.

The first end portion 207A of the cleaning element 207 is treaded around guide bodies 211, 212 and the second end portion 207B of the cleaning element 207 is treaded around a guide body 213. The guide bodies 211-213 of the cleaning element control mechanism 202 serve to constrain the respect one of the end portions 207A, 207B of the cleaning element 207 to be engaged against an exterior perimeter face of the rotatable body 204. In this manner, each of the end portion 207A, 207B of the cleaning element 207 wraps uniformly (e.g., snugly) around a face of the rotatable body 204 with little to no slack. The guide bodies 211-213 also serve to direct the central portion of the cleaning element 207 toward the distal end portion of the device 200.

As shown, this arrangement enables a length of the cleaning element 207 to be supplied from adjacent the second end portion 207B of the cleaning element 207 at the same or similar rate as it is taken up at the first end portion 207A of the cleaning element 207 as the rotatable body 204 is rotated in a counterclockwise direction. During such rotation (e.g., via manipulation of a user interface body that is directly or indirectly attached to the rotatable body 204), the first end portion 207A of the cleaning element 207 is wrapped onto the rotatable body 204 in a corresponding manner as the second end portion 207B of the cleaning element 207 is unwrapped from on the rotatable body 204 such that a retracting force is exerted on the first end portion 207A of the cleaning element 207 whereby a central portion of the cleaning element is correspondingly pulled around a support body at distal end of the cleaning device (see FIGS. 2-8 in regard to a central portion of cleaning element that is pulled around a support body at distal end of a cleaning device).

Movement of the cleaning element 207 is reversed when the rotatable body 204 is rotated in the opposite direction. This dual-direction cleaning element translation action of the cleaning element control mechanism 202 provides for both cleaning an imaging element and wrapping/unwrapping (i.e., supplying/taking-up) the cleaning element 207. In this manner, a length of material from which the cleaning element 207 is made can be used multiple times in a back and forth action to clean an imaging element.

Figure 10:
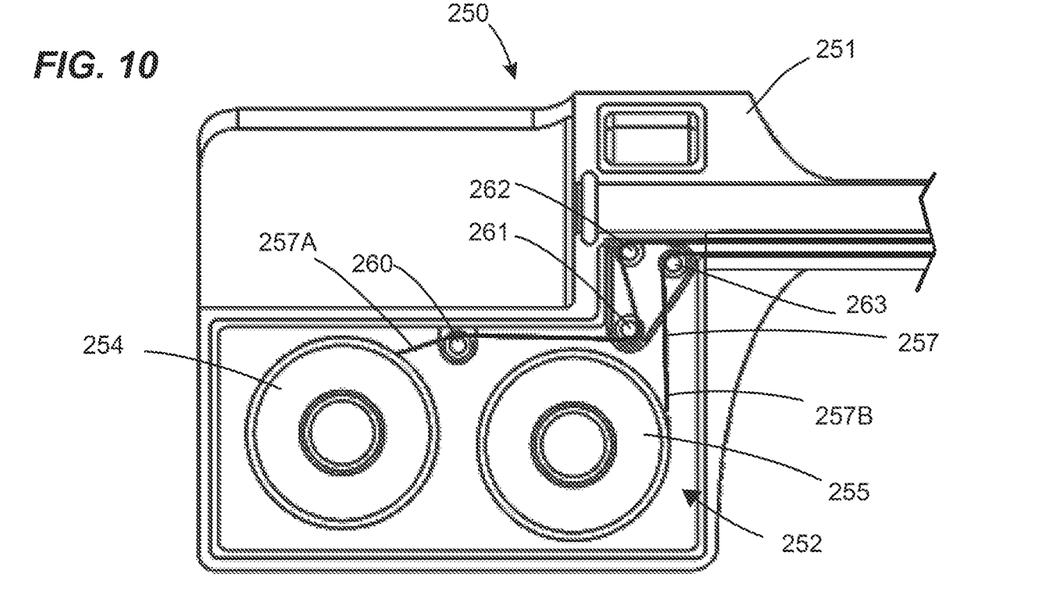
FIG. 10 is a diagrammatic view showing a cleaning element transport mechanism configured in accordance with a third embodiment of the disclosures made herein.

In another example, as shown in FIG. 10, a cleaning device 250 has a cleaning element control mechanism 252. The cleaning element control mechanism 252 includes a rotatable feed body 254 (i.e., a first rotatable body), a rotatable take-up body 255, and a cleaning element 257. The rotatable feed body 254 and the rotatable take-up body 255 are rotatably attached to a main body 251 of the device 250. The cleaning element 257 may be in the form of a length of material such as cloth, fabric, or other material or combinations of materials. The cleaning element 257 has free ends (i.e., cleaning element is not in the form of a band) whereby a first end portion 257A and a second end portion 257B are defined. The first end portion 257A of the cleaning element 257 is attached to the rotatable feed body 254 and the second end portion 257B of the cleaning element 257 is attached to the rotatable take-up body 255.

The first end portion 257A of the cleaning element 257 is treaded around guide bodies 260-262 and the second end portion 257B of the cleaning element 257 is treaded around a guide body 263. The guide bodies 260-263 of the cleaning element control mechanism 252 serve to constrain the respect one of the end portions 257A, 257B of the cleaning element 257 to be engaged against an exterior perimeter face of the respective one of the rotatable body 254, 255. In this manner, each of the end portion 257A, 257B of the cleaning element 257 wraps uniformly (e.g., snugly) around a face of the rotatable body 254 with little to no slack. The guide bodies 260-263 also serve to direct the central portion of the cleaning element 257 toward the distal end portion of the device 250.

A supply of the cleaning element 257 is wrapped onto the rotatable feed body 255. Rotating the take-up body 255 results in wrapping of the cleaning element 257 onto the rotatable take-up body 255 and feeding of the cleaning element 257 from the rotatable feed body 254. Depending on the user interface arrangement, the rotatable take-up body 255 and the rotatable feed body 254 may switch functionalities to thereby allow the cleaning element 257 to be translated in opposing directions (e.g., fed from the first rotatable body onto the second rotatable body and then fed from the second rotatable body onto the first rotatable body).

By rotating the rotatable take-up body 255 (e.g., via manipulation of a user interface body that is directly or indirectly attached to the rotatable take-up body 255), tension is applied to the cleaning element 207 such that a length of the cleaning element 257 is pulled from the rotatable feed body 254 and a central portion of the cleaning element 257 is correspondingly pulled around the support body at the distal end of the cleaning device 250 (see FIGS. 2-8 in regard to a central portion of cleaning element that is pulled around a support body at distal end of a cleaning device). In a particular implementation, the cleaning element 257 may only be fed from the first rotatable body onto the second rotatable body thereby allow for only unused cleaning element material 257 to be used for cleaning the imaging element.

Figure 11:
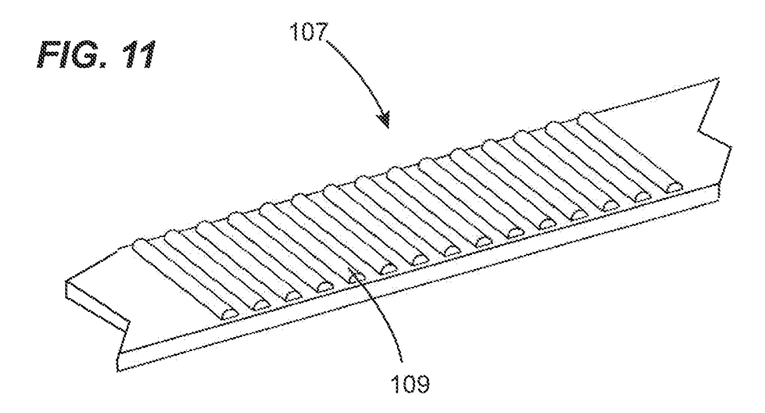
FIG. 11 is a fragmentary perspective view of an alternate cleaning band for an imaging element cleaning device in accordance with one or more embodiments of the disclosures made herein.

The cleaning element 107 may be made from an absorbent or otherwise contaminant-receptive material. Thus, in some embodiments, such material may attract contaminants on the imaging element of a visual scope and then fully or partially shed such contaminants (e.g., due to change in cleaning element geometry, due to one or more contaminant removal structure integral with the elongated tubular body 102, the control body 104, the main body 120 of the cleaning head 107, a combination thereof, or the like). The cleaning element 107 is not limited to any particular material or physical configuration so long as suitable imaging element cleaning performance is provided. For example as shown in FIG. 11, the cleaning element 107 may include one or more geometric surface structures 109 (ridges, dimples, dots, whiskers, etc.) to aid in achieving suitable cleaning performance and may be made from a material offering resilience (e.g., an elastomer, rubber, or the like). The cleaning element 107 may also be made of or include differentiated material types to aid in achieving suitable cleaning performance.

Figure 12:
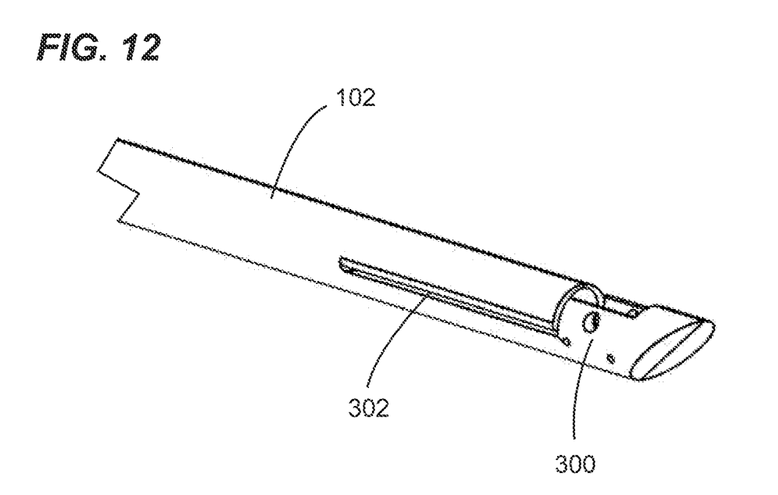
FIG. 12 is a fragmentary perspective view of a distal end portion for an imaging element cleaning device in accordance with one or more embodiments of the disclosures made herein.

As discussed above in reference to FIGS. 5-7, the cleaning device includes structure enabling the cleaning head 106 to move between its deployed orientation D2 and its retracted orientation R2. Specifically, a pivoting arrangement is used for enabling such movement. Alternatively, as shown in FIG. 12, the elongated tubular body 102 may include an integral cleaning head body 300 in place of the main body 120 discussed above, where integral cleaning head body 300 is resiliently displaceable through incorporation of a structure 302 (e.g., an elongated slot) enabling flexure of a portion of the elongated tubular body 102 comprising the integral cleaning head body 300.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A device operable to clean an imaging element of a visualization scope, comprising:
 a visualization scope engagement body;
 a cleaning element having a first end portion thereof located adjacent to a distal end of the visualization scope engagement body; and
 a cleaning head attached to the visualization scope engagement body at the distal end thereof, wherein the first end portion of the cleaning element is engaged with the cleaning head, wherein the cleaning head is movable between a deployed configuration relative to the visualization scope engagement body and a retracted configuration relative to the visualization scope engagement body and wherein a centerline longitudinal axis of the visualization scope engagement body extends through the cleaning head when the cleaning head is in the deployed configuration and does not extend through the cleaning head when the cleaning head is in the retracted configuration;
wherein:
 the cleaning element has a second end portion and a central portion extending between the first and second end portions;
 the second end portion is located adjacent to a proximate end of the visualization scope engagement body;
 at least a portion of the central portion extends through a guide passage of the visualization scope engagement body;
 the visualization scope engagement body includes a cleaning element guide body at the distal end portion thereof;
 a pivot axis about which the cleaning head is pivotable relative to the visualization scope engagement body extends through the cleaning element guide body;
 the cleaning element extends over the cleaning element guide body;
 the cleaning head includes a main body pivotably attached to the visualization scope engagement body at the distal end thereof and a first cleaning element support body attached to the main body;
 the first end portion of the cleaning element extends around the first cleaning element support body; and
 the first cleaning element support body is rotatably attached to the main body for enabling the first cleaning element support body to rotate relative to the main body.

2. The device of claim 1 wherein the centerline longitudinal axis of the visualization scope engagement body lies between an axis about which the first cleaning element support rotates relative to the main body when the cleaning head is in the deployed configuration and a pivot axis about which the cleaning head pivots relative to the visualization scope engagement body.

3. A device operable to clean an imaging element of a visualization scope, comprising:
 a visualization scope engagement body;
 a cleaning element having a first end portion thereof located adjacent to a distal end of the visualization scope engagement body; and
 a cleaning head attached to the visualization scope engagement body at the distal end thereof, wherein the first end portion of the cleaning element is engaged with the cleaning head, wherein the cleaning head is movable between a deployed configuration relative to the visualization scope engagement body and a retracted configuration relative to the visualization scope engagement body and wherein a centerline longitudinal axis of the visualization scope engagement body extends through the cleaning head when the cleaning head is in the deployed configuration and does not extend through the cleaning head when the cleaning head is in the retracted configuration;
wherein:
 the cleaning head includes a main body pivotably attached to the visualization scope engagement body at the distal end thereof and a first cleaning element support body attached to the main body;
 the first end portion of the cleaning element extends around the first cleaning element support body;
 a centerline longitudinal axis of a central passage of the visualization scope engagement body lies between an axis about which the first cleaning element support body rotates relative to the main body when the cleaning head is in the deployed configuration and a pivot axis about which the cleaning head pivots relative to the visualization scope engagement body;

the cleaning element has a second end portion and a central portion extending between the first and second end portions;

the second end portion is located adjacent to a proximate end of the visualization scope engagement body;

at least a portion of the central portion extends through a guide passage of the visualization scope engagement body;

the visualization scope engagement body includes a cleaning element guide body at the distal end thereof;

the pivot axis about which the cleaning head pivots relative to the visualization scope engagement body extends through the cleaning element guide body; and the cleaning element extends over the cleaning element guide body.

4. The device of claim 3 wherein the first cleaning element support body is rotatably attached to the main body.

5. A device operable to clean an imaging element of a visualization scope, comprising:

a visualization scope engagement body;

a cleaning element having a first end portion thereof located adjacent to a distal end of the visualization scope engagement body;

a cleaning head attached to the visualization scope engagement body at the distal end thereof, wherein the first end portion of the cleaning element is engaged with the cleaning head, wherein the cleaning head is movable between a deployed configuration relative to the visualization scope engagement body and a retracted configuration relative to the visualization scope engagement body and wherein a centerline longitudinal axis of the visualization scope engagement body extends through the cleaning head when the cleaning head is in the deployed configuration and does not extend through the cleaning head when the cleaning head is in the retracted configuration; and a drive unit at a proximate end of the visualization scope engagement body, wherein the drive unit includes a second cleaning element support body and an actuation member coupled to the second cleaning element support body, wherein movement of the actuation member causes an associated movement of the second cleaning element support body, wherein a second end portion of the cleaning element is engaged with the second cleaning element support body such that movement of the actuation member from a present position to a different position than the present position causes a corresponding movement of the cleaning element relative to the cleaning head.

6. The device of claim 5 wherein:

the cleaning element has a second end portion and a central portion extending between the first and second end portions;

the second end portion is located adjacent to a proximate end of the visualization scope engagement body; and at least a portion of the central portion extends through a guide passage of the visualization scope engagement body.

7. The device of claim 5 wherein the cleaning head is pivotably attached to the visualization scope engagement body for enabling the cleaning head to pivot between the deployed configuration relative to the visualization scope engagement body and the retracted configuration relative to the visualization scope engagement body.

8. The device of claim 5 wherein:

the cleaning head includes a main body pivotably attached to the visualization scope engagement body at the distal end thereof and a first cleaning element support body attached to the main body;

the first end portion of the cleaning element extends around the first cleaning element support body; and the first cleaning element support body is rotatably attached to the main body for enabling the first cleaning element support body to rotate relative to the main body.

9. A device operable to clean an imaging element of a visualization scope, comprising:

a visualization scope engagement body with which an extension portion of the visualization scope is engageable for enabling the extension portion to be moveable between a plurality of positions relative to a distal end of the visualization scope engagement body;

a cleaning head attached to the visualization scope engagement body at the distal end thereof, wherein the cleaning head is movable between a deployed configuration relative to the visualization scope engagement body and a retracted configuration relative to the visualization scope engagement body in conjunction with movement of the extension portion of the visualization scope between a first one of the positions and a second one of the positions different than the first one of the positions;

a cleaning element having a first end portion thereof located adjacent to the distal end of the visualization scope engagement body, wherein the first portion of the cleaning element is engaged with the cleaning head, wherein the cleaning element is in contact with the imaging element when the cleaning head is in the deployed configuration and is displaced away from being in contact with the imaging element when the cleaning head is in the retracted configuration; and a drive unit at a proximate end of the visualization scope engagement body, wherein the drive unit includes a second cleaning element support body and an actuation member coupled to the second cleaning element support body, wherein movement of the actuation member causes an associated movement of the second cleaning element support body, wherein a second end portion of the cleaning element is engaged with the second cleaning element support body such that movement of the actuation member from a present position to a different position than the present position causes a corresponding movement of the cleaning element relative to the cleaning head.

10. The device of claim 9 wherein:

the cleaning element has a central portion extending between the first and second end portions;

the second end portion is located adjacent to a proximate end of the visualization scope engagement body; and at least a portion of the central portion extends through a guide passage of the visualization scope engagement body.

11. The device of claim 10 wherein the cleaning head is pivotably attached to the visualization scope engagement body for enabling the cleaning head to pivot between the deployed configuration relative to the visualization scope engagement body and the retracted configuration relative to the visualization scope engagement body.

12. The device of claim 10 wherein:
the cleaning head includes a main body pivotably attached to the visualization scope engagement body at the distal end thereof and a first cleaning element support body attached to the main body;
the first end portion of the cleaning element extends around the first cleaning element support body; and
the first cleaning element support body is rotatably attached to the main body for enabling the first cleaning element support body to rotate relative to the main body.

13. A device operable to clean an imaging element of a laparoscope, comprising:
a tubular body having a central passage within which an extension portion of a laparoscope is slidably engageable for enabling the tubular body to be axially moveable between a retracted configuration relative to the laparoscope and a deployed configuration relative to the laparoscope;
a cleaning head including a main body pivotably attached to the tubular body at a distal end thereof and a first cleaning element support body attached to the main body, wherein the cleaning head is movable between a deployed configuration relative to the tubular body and a retracted configuration relative to the tubular body, wherein a centerline longitudinal axis of the central passage extends through the first cleaning element support body when the cleaning head is in the deployed configuration thereof and does not extend through the first cleaning element support body when the cleaning head is in the retracted configuration thereof and wherein the cleaning head is in the deployed configuration thereof when the tubular body is in the deployed configuration thereof and is in the retracted configuration thereof when the tubular body is in the retracted configuration thereof;
a drive unit at a proximate end of the tubular body, wherein the drive unit includes a second cleaning element support body and an actuation member coupled to the second cleaning element support body and wherein movement of the actuation member causes an associated movement of the second cleaning element support body; and
a cleaning element having a first end portion engaged with the first cleaning element support body and a second end portion engaged with the second cleaning element support body such that movement of the cleaning head between the deployed configuration relative to the tubular body and the retracted configuration relative to the tubular body causes corresponding movement of the first end portion of the cleaning element and such that movement of the actuation member from a present position to a different position than the present position causes a corresponding movement of the cleaning element relative to the main body of the cleaning head.

14. The device of claim 13 wherein:
the tubular body includes a cleaning element guide body at the distal end portion thereof;
a pivot axis about which the main body of the cleaning head is pivotable relative to the tubular body extends through the cleaning element guide body; and
the cleaning element extends over the cleaning element guide body.

15. The device of claim 14 wherein:
the first end portion of the cleaning element extends around the first cleaning element support body; and
the first cleaning element support body is rotatably attached to the main body for enabling the first cleaning element support body to rotate relative to the main body.

16. The device of claim 13 wherein the centerline longitudinal axis of the central passage of the tubular body lies between an axis about which the first cleaning element support body is rotatable relative to the main body when the cleaning head is in the deployed configuration and a pivot axis about which the cleaning head is pivotable relative to the tubular body.

* * * * *